United States Patent
Neyens et al.

(10) Patent No.: US 7,370,544 B2
(45) Date of Patent: May 13, 2008

(54) DEVICE FOR PERFORMING MEASUREMENTS AND/OR TAKING SAMPLES IN MOLTEN METALS

(75) Inventors: Guido Jacobus Neyens, Opoeteren (BE); Shaun Andrew Bell, Zelionople, PA (US)

(73) Assignee: Heraeus Electro-Nite International N.V., Houthalen (BE)

(*) Notice: Subject to any disclaimer, the term of this patent is extended or adjusted under 35 U.S.C. 154(b) by 128 days.

(21) Appl. No.: 11/153,277

(22) Filed: Jun. 15, 2005

(65) Prior Publication Data

US 2005/0279183 A1 Dec. 22, 2005

(30) Foreign Application Priority Data

Jun. 16, 2004 (DE) .................. 10 2004 028 789

(51) Int. Cl.
G01N 1/12 (2006.01)
G01N 33/20 (2006.01)

(52) U.S. Cl. .................. 73/864.59; 73/64.56

(58) Field of Classification Search ............ 73/864.59, 73/19.07, 61, 42, 64.56, 864.73, 866.5; 266/99; 374/139
See application file for complete search history.

(56) References Cited

U.S. PATENT DOCUMENTS

| | | | |
|---|---|---|---|
| 3,698,954 A | | 10/1972 | Jones |
| 4,141,249 A | * | 2/1979 | Ishikawa et al. ......... 73/863.11 |
| 4,320,668 A | * | 3/1982 | Honda et al. ............ 73/863.11 |
| 4,438,653 A | | 3/1984 | Beentjes |
| 4,566,343 A | * | 1/1986 | Theuwis et al. ......... 73/864.59 |
| 4,912,989 A | * | 4/1990 | Cassidy .................... 73/866.5 |
| 5,429,010 A | * | 7/1995 | Lohndorf et al. .......... 73/866.5 |
| 5,515,739 A | * | 5/1996 | Baerts ..................... 73/864.55 |
| 7,272,983 B2 | * | 9/2007 | Caderas ................... 73/866.5 |
| 2007/0137324 A1 | * | 6/2007 | Neyens ..................... 73/866.5 |

FOREIGN PATENT DOCUMENTS

| | | |
|---|---|---|
| CN | 1088839 C | 8/2002 |
| DE | 1 921 322 | 12/1969 |
| DE | 36 41 225 A1 | 6/1987 |
| DE | 2718860 C2 | 9/1987 |
| DE | 43 06 332 A1 | 8/1994 |
| EP | 0 069 433 A1 | 1/1983 |
| EP | 0 143 498 A2 | 6/1985 |
| EP | 0 143 498 B1 | 3/1987 |
| JP | 53-79703 | 7/1978 |
| JP | 61-48104 B2 * | 10/1986 |
| JP | 01073014 A * | 3/1989 |
| JP | 01132711 A * | 5/1989 |
| JP | 02263159 A * | 10/1990 |
| JP | 03048156 A * | 3/1991 |
| JP | 07218155 A * | 8/1995 |
| JP | 2001026809 A * | 1/2001 |
| WO | WO 03/064714 A1 | 8/2003 |

\* cited by examiner

Primary Examiner—Thomas P Noland
(74) Attorney, Agent, or Firm—Panitch Schwarze Belisario & Nadel LLP

(57) ABSTRACT

A device is provided for performing measurements and/or taking samples in molten metals with a sublance, which has a sublance body, on whose one end a lance holder is arranged for receiving an immersion probe. The sublance body is movably connected to the lance holder and/or the lance holder has several parts relatively movable to each other.

3 Claims, 3 Drawing Sheets

DEVICE FOR PERFORMING MEASUREMENTS AND/OR TAKING SAMPLES IN MOLTEN METALS

BACKGROUND OF THE INVENTION

The invention relates to a device for performing measurements and/or taking samples in molten metals with a sublance, which has a sublance body, on whose one end a lance holder is arranged for receiving an immersion probe.

Such devices are sufficiently well known to those skilled in the art. They are used for measurements or taking samples in molten metals. Such sampling is partially automated, wherein a sublance is dipped into a melt container, after which the immersion probe arranged on the sublance is discarded, because it is used up, and a new immersion probe is placed on the sublance. In order to automate this procedure, the sublance must be able to be positioned exactly over a probe storage container.

In practice, however, it has been shown that, due to the loads exerted on a sublance during use, these sublances become slightly deformed, so that the lance holder can no longer be placed exactly over an immersion probe and the probe cannot be received without problems. The immersion probes placed on the sublances do not have the same exact length. In particular, the contact part housed in the carrier tube cannot always be reached at the same depth by the counter contact in the sublance. As a result, splashes of the molten metal frequently settle onto parts of the sublance, which must remain free for forming the contact, so that trouble-free placement of the immersion probes is impossible. This can disrupt the entire steel making process.

Sublances are known, for example, from European published patent application EP 69 433 A1. Here, an attempt is made to counteract the deformation of the sublance during the operation by rotating the sublance. The arrangement and function of sublances is further described in German published patent application DE 43 06 332 A1. Here, the exchanging procedure of the sample probes is also disclosed. Another sublance is known from European Patent EP 143 498 B1. The sublance described here has a seal, for example a rubber ring, at connection points, which prevents liquid metal from being able to penetrate into the mechanism.

The invention is based on the problem of improving the known sublances and especially enhancing the fail-safe means in automatic operation.

BRIEF SUMMARY OF THE INVENTION

The problem is solved for the invention characterized above in that on the lance holder a contact piece is arranged for making contact with signal lines of the immersion probe, furthermore in that the sublance body is movably connected to the lance holder or to a part thereof and/or in that the lance holder has several parts relatively movable to each other, whereby the contact piece is arranged to be movable relative to the sublance. The sublance is pushed tight onto the upper part of the lance holder and is preferably held so that it cannot move. The lower part of the lance holder is movable with the contact piece, so that the probe can be brought into contact with the contact piece. The lance holding can thereby adapt to the already set sensor, so that a sufficient contact is possible even for slightly deformed components or even when molten metal adheres to the sublance.

Different insertion depths of the sublance into the carrier tube of the immersion probe are likewise compensated in this manner. Preferably, the sublance body with the lance holder and/or the parts of the lance holder are arranged to be movable in the axial direction and/or in the radial direction. Furthermore, it is advantageous when the axial movement and the radial movement are realized by pairs of connection parts that are different from each other, in order to obtain the highest possible flexibility and adaptability. Especially for adhesion of molten metal on the sublance or for differently arranged contact parts of the immersion probe, an axial movement is important, in order to guarantee the correct contact with the immersion probe. In particular, it is advantageous when the movement is realized by elastic parts arranged between rigid parts, wherein the elastic parts can be formed as a spring, for example as a coil spring, or as an elastic ring.

Furthermore, it is useful if a part of the lance holder has a receiving hole, in which a peg of a second part of the lance holder can move in the axial direction, wherein a coil spring is arranged between the first and the second parts of the lance holder. For this purpose, it is advantageous if the coil spring is arranged between a stopping surface arranged at the front end or on the peripheral surface of the peg and a second stopping surface is arranged at or in the hole. The components guaranteeing the movement are thereby protected themselves.

It is useful if a part of the lance holder has a receiving hole, in which a peg of a second part of the lance holder is movable in the radial direction, wherein at least one elastic ring is arranged between the first and the second parts of the lance holder. The elastic ring can be arranged advantageously in the radial direction between the two parts of the lance holder.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
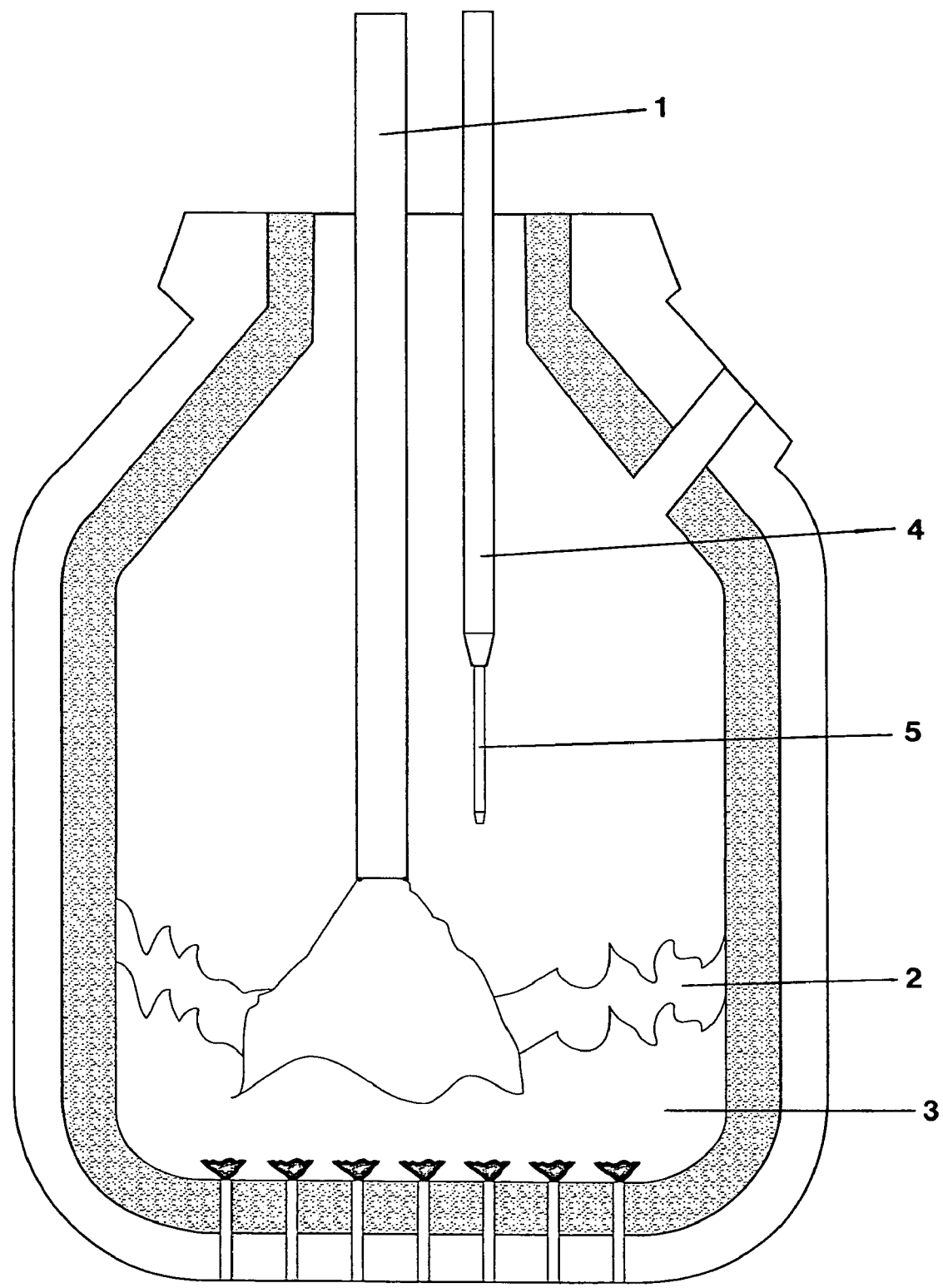
FIG. 1 is a schematic cross-sectional view of a converter furnace with a sublance.

In the converter furnace shown in FIG. 1 a blowing lance 1 is arranged, which blows oxygen into the molten slag 2 or molten steel 3. Next to this lance a sublance 4 with an immersion probe 5 is arranged. The sublance 4 travels from above into the converter furnace until the immersion probe 5 is immersed in the molten steel 3. After the measurement, the sublance is pulled up; the immersion probe 5 is destroyed.

If the probe is designed as a measurement probe, then the measurement is performed during the immersion in the molten steel 3. A sample chamber arranged in the immersion probe 5 was filled while in the molten steel 3. The sample chamber is removed from the discarded immersion probe 5, and the sample can be analyzed. For the next measurement, another immersion probe 5 is taken from a storage container, usually mechanically mounted on the sublance 4, and inserted into the converter furnace for the measurement.

Figure 2:
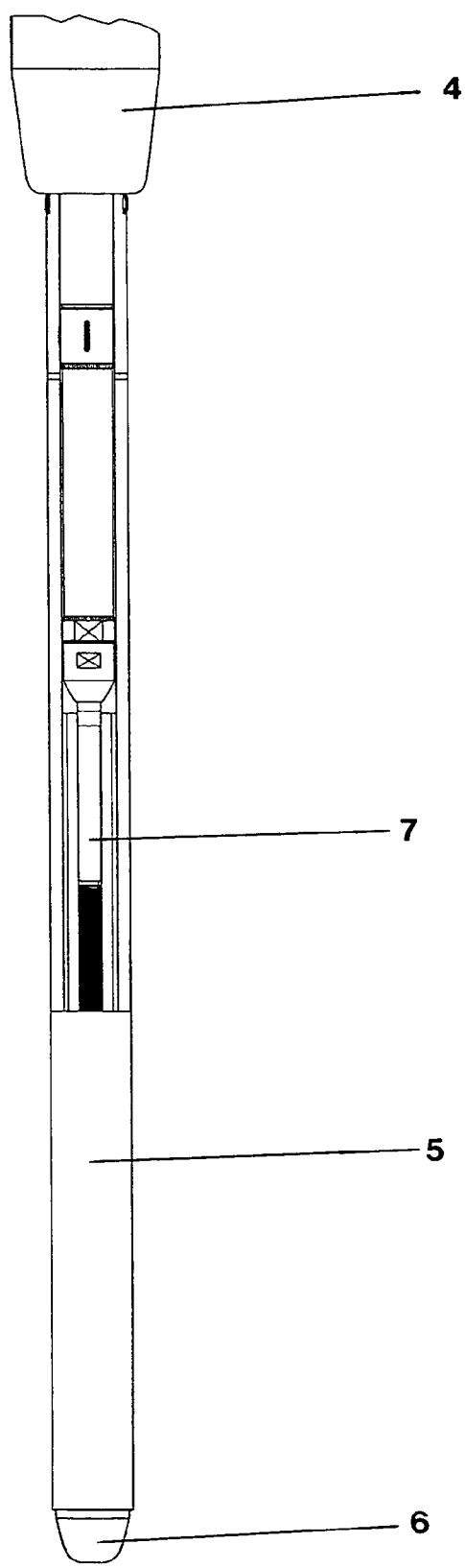
FIG. 2 is a partially broken away schematic side longitudinal view of a sublance with lance holder and immersion probe according to one embodiment of the invention.

FIG. 2 shows the immersion probe 5 arranged at the lower end of the sublance 4. The immersion probe 5 has an immersion end, which is protected from the slag layer 2 lying on the molten steel 3 by a cap 6, which exposes the sensor or the sample chamber only after being immersed in the molten steel 3. The immersion probe 5 is fixed to the sublance 4 by means of the lance holder. The signal lines of the immersion probe 5 are contacted by a contact piece 7 arranged on the lance holder, so that the measurement signals can be led back through the sublance 4 to an analysis unit.

Figure 3:
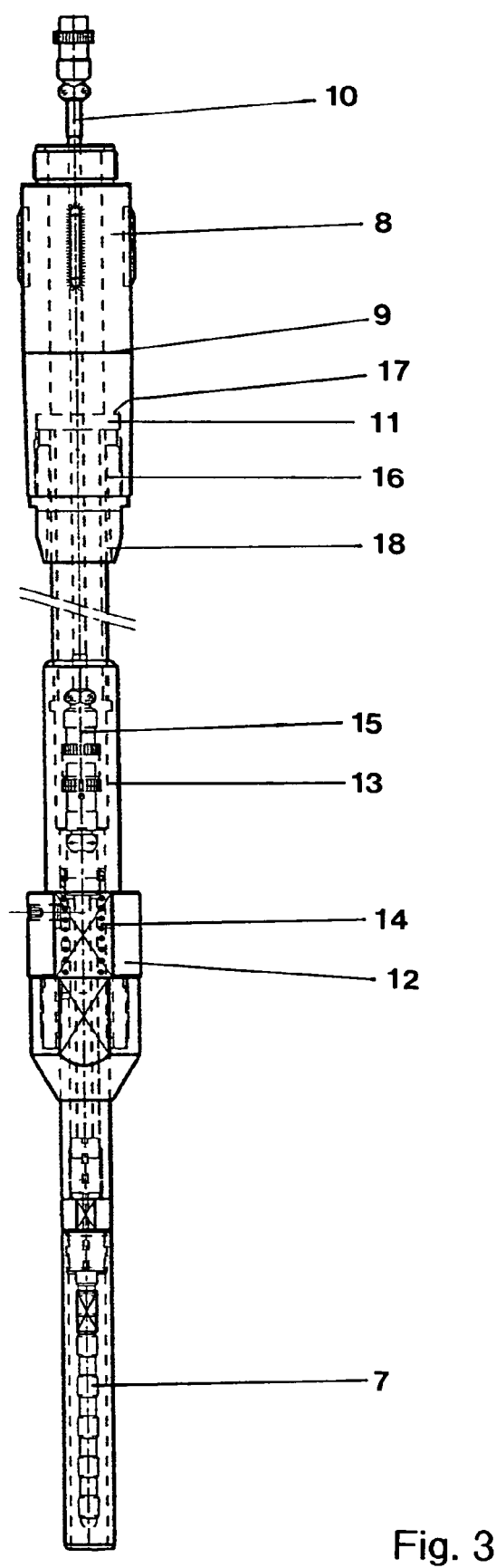
FIG. 3 is a truncated schematic side longitudinal view of one embodiment of a lance holder in detail.

In FIG. 3 the lance holder is shown in detail. The lance holder is a reusable part of the sublance 4. It is used for holding the immersion probe 5 and as a contact connection with the immersion probe 5. The lance holder is connected to the water-cooled part of the sublance 4. The water cooling is not explained in more detail in the Figures. It is sufficiently well known from the prior art (for example, EP 69 433).

The lance holder is arranged with its upper part 8 rigidly in the sublance 4 and with its lower part, beginning approximately at the separating line 9, in the immersion probe 5. In this way, the contact piece 7 guarantees the electrical contact with the signal lines of the immersion probe 5. The conductance of the electrical signals and their transmission to a measurement or analysis station take place through the lance cable 10, which is arranged at the upper end of the lance holder and which passes through the sublance 4.

A rubber ring 11 is arranged in the upper region of the lance holder. The rubber ring 11 enables the lower part of the lance holder to move in both the radial direction and the axial direction relative to the upper part 8. The rubber ring 11 is held against a stop 17 by a screw 16. The screw 16 has a through hole 18 in the axial direction, which expands conically in the direction towards the contact piece 7. The upper part 8 of the sublance 4 is thereby movable relative to the lower part in the radial direction and also slightly in the axial direction. Instead of a rubber ring 11, a metal spring, for example a coil spring, can also be used.

The lower part of the lance holder with the contact piece 7 has a sealing sleeve 12, into which a guide tube 13 projects. A coil spring 14 is arranged in the longitudinal direction between the guide tube 13 and an inner stopping surface of the sealing sleeve 12. Movement of the contact piece 7 with the sealing sleeve 12 along the guide tube 13 is thereby guaranteed. This movement always ensures a secure contact between the signal lines of the immersion sensor 5 and the contact piece 7, even with different lengths of the various immersion sensors 5, which are mounted on the lance holder.

A secure contact is then guaranteed even if foreign matter, such as molten metal or slag, has become fixed on the lance holder. This can occur in the upper part of the lance holder, where the sublance 4 and the immersion probe 5 contact each other. Even in such a case of contamination, a reliable contact between the contact piece 7 and the signal lines of the immersion probe 5 is guaranteed by the spring 14. The spring 14 preferably has a spring tension that is greater than the attachment force of the contact piece 7 on the so-called connector within the immersion probe 5, with whose help the signal lines make contact with the contact piece.

Within the guide tube 13 coupling elements 15 can be provided, by which the lance cable 10 is connected to the contact piece 7. In the manner shown, the contact piece 7 is arranged to be movable both in the longitudinal and the radial directions relative to the sublance 4, and therefore can then be connected to the signal lines of the immersion probe, even if the lower end of the sublance 4 carrying the lance holder is slightly bent. A secure, mechanical holding of the immersion probe 5 is possible as well in practically every conceivable case.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for at least one of performing measurements and taking samples in molten metals, comprising
   a sublance having a sublance body,
   a lance holder arranged on one end of the sublance body for receiving an immersion probe,
   a contact piece arranged on the lance holder for making contact with signal lines for the immersion probe,
   wherein at least one of (a) the sublance body is movably connected to the lance holder and (b) the lance holder has several parts movable relative to each other, such that the contact piece is arranged to be movable relative to the sublance body, wherein at least one of the sublance body with the lance holder and the parts of the lance holder is movable in at least one of an axial or radial direction, and wherein the axial movement and the radial movement are realized by pairs of connection parts that are different from each other.

2. The device according to claim 1, wherein the movement is realized by elastic parts arranged between rigid parts.

3. The device according to claim 2, wherein the elastic parts are formed as coil springs or elastic rings.

\* \* \* \* \*